(12) United States Patent
Ryu et al.

(10) Patent No.: US 11,485,716 B2
(45) Date of Patent: Nov. 1, 2022

(54) COMPOUNDS USEFUL FOR TREATMENT OR PREVENTION OF MUSCULAR DYSTROPHY AND DERIVATIVES FOR TREATMENT, AMELIORATION OR PREVENTION OF MUSCULAR DYSTROPHY IN MEDICINAL USE THEREOF

(71) Applicant: J2H BIOTECH INC., Gyeonggi-do (KR)

(72) Inventors: Hyung-Chul Ryu, Gyeonggi-do (KR); Jae-Sun Kim, Gyeonggi-do (KR); Jee-Woong Lim, Gyeonggi-do (KR); Ju-Young Lee, Gyeonggi-do (KR); Wenling Song, Gyeonggi-do (KR); Tae-Gon Kim, Chungcheongbuk-do (KR)

(73) Assignee: J2H BIOTECH INC., Gyeonggi-do (KR)

( * ) Notice: Subject to any disclaimer, the term of this patent is extended or adjusted under 35 U.S.C. 154(b) by 0 days.

(21) Appl. No.: 17/413,608

(22) PCT Filed: Dec. 24, 2019

(86) PCT No.: PCT/KR2019/018434
§ 371 (c)(1),
(2) Date: Jun. 14, 2021

(87) PCT Pub. No.: WO2020/138935
PCT Pub. Date: Jul. 2, 2020

(65) Prior Publication Data
US 2022/0033366 A1    Feb. 3, 2022

(30) Foreign Application Priority Data
Dec. 27, 2018   (KR) .................. 10-2018-0170965

(51) Int. Cl.
*C07D 271/06* (2006.01)
(52) U.S. Cl.
CPC .................. *C07D 271/06* (2013.01)

(58) Field of Classification Search
CPC .................................................... C07D 271/06
See application file for complete search history.

(56) References Cited

U.S. PATENT DOCUMENTS 6,992,096 B2    1/2006 Karp et al.
2011/0195932 A1    8/2011 Wynne et al.

FOREIGN PATENT DOCUMENTS

WO    WO-2016/198971 A1    12/2016

OTHER PUBLICATIONS

International Search Report from corresponding PCT Application No. PCT/KR2019/018434, dated Apr. 21, 2020.
Namgoong, J., H., et al.; "Clinical potential of ataluren in the treatment of Duchenne muscular dystrophy", Degenerative Neurological and Neuromuscular Disease, 2016, vol. 6, pp. 37-48.
Payne, E. T., et al.; "Nutritional therapy improves function and complements corticosteroid intervention in mdx mice", Muscle & Nerve, 2006, vol. 33, pp. 66-77.
Offord, C.; "Trial of Gene Therapy for Duchenne Muscular Dystrophy Put on Hold", The Scientist. Muscular Dystrophy News Today, 2017, pp. 1-2.
Wu, H., et al.; "Effect of beta-hydroxy-beta-methylbutyrate supplementation on muscle loss in older adults: A systematic review and meta-analysis", Archives of Gerontology and Geriatrics 61 (2015) 168-175.
Landi, F., et al.; "Sarcopenia: An Overview on Current Definitions, Diagnosis and Treatment", Current Protein and Peptide Science, 2018, vol. 19, No. 00.

*Primary Examiner* — Shawquia Jackson
(74) *Attorney, Agent, or Firm* — Harness, Dickey & Pierce, P.L.C.

(57) ABSTRACT

The present invention relates to a novel compound and a medicinal use of the novel compound. In particular, the present invention relates to a novel compound useful for the treatment and/or prevention of muscular dystrophy, including Duchenne muscular atrophy, and a medicinal use of the novel compound.

8 Claims, 1 Drawing Sheet

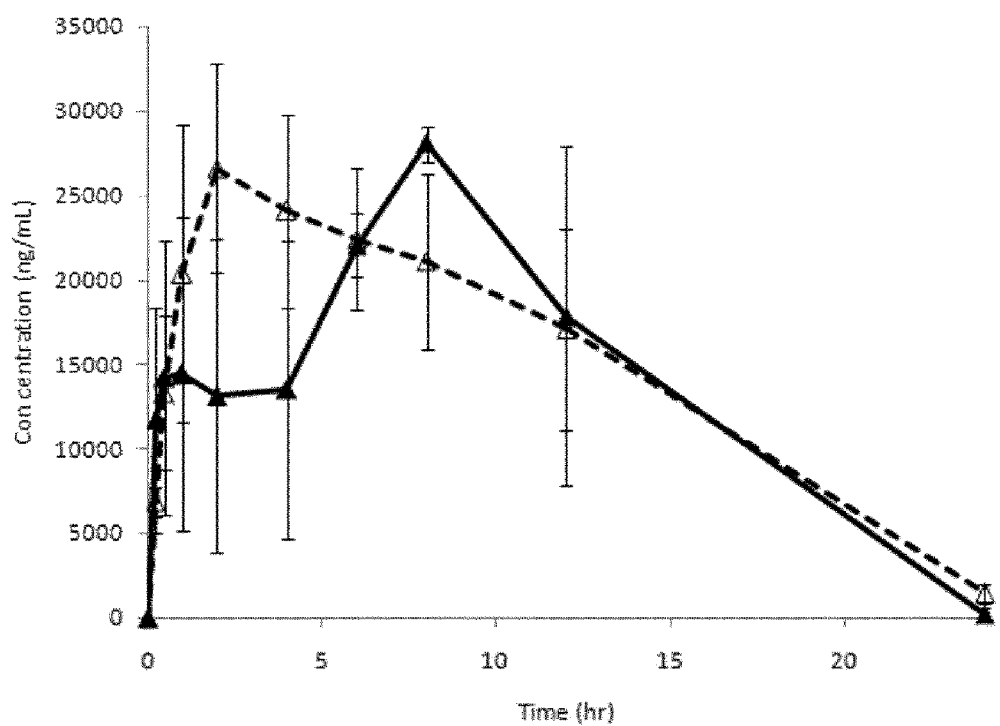

COMPOUNDS USEFUL FOR TREATMENT OR PREVENTION OF MUSCULAR DYSTROPHY AND DERIVATIVES FOR TREATMENT, AMELIORATION OR PREVENTION OF MUSCULAR DYSTROPHY IN MEDICINAL USE THEREOF

CROSS-REFERENCE TO RELATED APPLICATIONS

This application is a national phase application of PCT Application No. PCT/KR2019/018434, filed on Dec. 24, 2019, which claims priority to Korean Patent Application No. 10-2018-0170965, filed on Dec. 27, 2018. The entire disclosure of the applications identified in this paragraph is incorporated herein by reference.

TECHNICAL FIELD

The present invention relates to novel compounds effective for treatment or prevention of (progressive) muscular dystrophy including Duchenne muscular dystrophy. The present invention also relates to medical use of a compound having a specific structure for treatment or prevention of muscular dystrophy.

BACKGROUND ART

Muscular dystrophy is a series of genetic diseases belonging to congenital myopathy, and clinically it shows progressive muscle weakness and muscle atrophy. Duchenne muscular atrophy with sex chromosomal inheritance is a representative disease among them, and it occurs with a frequency of 1 out of 3500 male children. The main symptoms are usually muscle weakness of the proximal muscles first, and it is difficult to get up from a lying position, get up from a chair, and raise an object, and it may be accompanied by cardiomyopathy and muscle tension reaction. The area where muscular dystrophy mainly occurs is the limbs, and as the muscle is degenerated, the muscle itself is changed to fat or connective tissue, and the function of generating strength by contraction and relaxation of the muscle is reduced. The onset of the disease is characterized by a very rapid and rapid progression.

A protein called dystrophin exists in muscles to maintain function. In particular, in the case of Duchenne muscular dystrophy (DMD), a lack of this protein due to genetic changes causes muscle weakness. Specifically, mutation of a dystrophin gene called locus Xp21 present on the X chromosome causes a decrease in dystrophin concentration and mitochondrial damage in muscle cells due to excessive calcium.

Meanwhile, as a therapeutic agent for DMD developed as a low molecular weight compound, ataluren (trade name: Translarna, U.S. Pat. No. 6,992,096) has been approved in Europe. This compound acts directly on ribosome during the expression of the mutated corresponding gene, making it less sensitive to the ribosome's abnormal stop codon recognition, so that the sub-step of protein synthesis through messenger RNA (mRNA) proceeds relatively normally. By doing so, it has a mechanism to induce production of a protein having a function similar to that of the protein produced by normal gene expression.

Meanwhile, ataluren was conditionally approved as a DMD treatment for patients over 5 years of age with gait impairment in Europe, whereas the US FDA has concluded that it is difficult to believe that the efficacy of the same drug has been substantially proven (Reference: Muscular Dystrophy News Today, 2017. 10). This means that efficient reconstitution of clinical trials is required, and at the same time, more reliable expression of drug efficacy is required.

SUMMARY

Technical Problem

Therefore, the problem to be solved by the present invention is to provide a new compound that is more effective than ataluren and its medical use for treatment and prevention of muscular dystrophy.

Technical Solution

In order to solve the above problem, the present disclosure provides a compound represented by the following Chemical Formula 1.

[Chemical Formula 1]

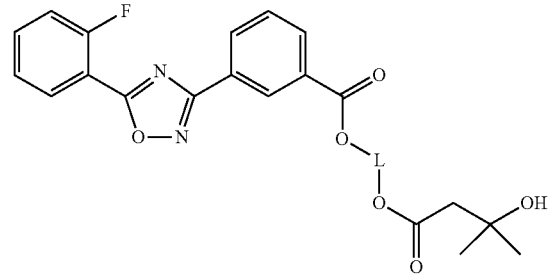

In the Chemical Formula 1,

L is selected from the group consisting of straight or branched alkyl having 1 to 3 carbon atoms and benzyl.

The novel compound according to the present invention improves bioavailability, absorption rate, drug effect onset time, crystallinity, physicochemical properties, etc. compared to ataluren by additionally introducing a functional group of a specific structure to the existing ataluren. In addition, the introduced structure can be separated in the body into beta-hydroxy beta-methyl butyric acid (HMB), which is a substance that has been applied in clinical trials for treatment of sarcopenia and is also an endogenous substance biosynthesized from L-leucine, an amino acid. The HMB is known as a substance that can prevent muscle atrophy as well as increase muscle mass when taken from outside (Archives of Gerontology and Geriatrics, 2015, 61, 168; Current Protein and Peptide Science, 2017, 18). Thus, HMB is a substance that can be further helpful for the purpose of the present invention of treating or preventing muscular dystrophy.

That is, the present invention utilizes pharmacological effects of both ataluren and HMB and combines them to have a specific structure, which improves various aspects such as bioavailability, absorption rate, drug effect onset time, physicochemical properties, crystallinity, etc. Such structure also is possible to fundamentally prevent various problems such as drug interaction and stability degradation that may occur when included separately.

In one embodiment of the present invention, the compound is 1-(3-hydroxy-3-methylbutanoyloxy)ethyl 3-(5-(2-fluorophenyl)-1,2,4-oxadiazol-3-yl)benzoate;

(3-hydroxy-3-methylbutanoyloxy)methyl 3-(5-(2-fluorophenyl)-1,2,4-oxadiazol-3-yl)benzoate;

2-(3-hydroxy-3-methylbutanoyloxy)ethyl 3-(5-(2-fluorophenyl)-1,2,4-oxadiazol-3-yl)benzoate; or 4-(3-hydroxy-3-methylbutanoyloxy)benzyl 3-(5-(2-fluorophenyl)-1,2,4-oxadiazol-3-yl)benzoate.

As used herein, the phrase "compound(s) of this/the invention" includes any compound(s) of Chemical Formula 1, as well as clathrates, hydrates, solvates, or polymorphs thereof.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

The present invention also provides a pharmaceutical composition for treating or preventing muscular dystrophy, particularly progressive muscular dystrophy, comprising the compound according to the present invention as an active ingredient. In one embodiment of the present invention, the muscular dystrophy is Duchenne muscular atrophy.

As used herein, the term "treatment" refers to any action in which symptoms of muscular dystrophy are eradicated, controlled, eliminated, controlled, improved, or cured by administration of the composition according to the present invention. The "improvement" refers to any action in which the degree of (progressive) muscular dystrophy is reduced, improved, or progress is delayed by administration of the composition according to the present invention.

As used herein, the term "prevention" means prevention of the recurrence of (progressive) muscular dystrophy or prevention of expansion or outbreak of muscular dystrophy by administration of the composition according to the present invention.

As used herein, the term "effective amount" refers to an amount of a compound of the present invention sufficient to treat muscular dystrophy, slow or minimize the expansion of muscular dystrophy, or provide a therapeutic benefit in the treatment or management of muscular dystrophy.

The pharmaceutical composition according to the present invention may comprise the compound represented by Chemical Formula 1 alone or may additionally comprise one or more pharmaceutically acceptable carriers, excipients or diluents.

As the pharmaceutically acceptable carrier, for example, a carrier for oral administration or a carrier for parenteral administration may be used. Carriers for oral administration may include lactose, starch, cellulose derivatives, magnesium stearate, stearic acid, and the like. In addition, carriers for parenteral administration may include water, suitable oil, saline, aqueous glucose and glycol, and the like, and may further include stabilizers and preservatives. Suitable stabilizers may be antioxidants such as sodium hydrogen sulfite, sodium sulfite or ascorbic acid. Suitable preservatives may be benzalkonium chloride, methyl- or propyl-paraben and chlorobutanol. Other pharmaceutically acceptable carriers well known to those skilled in the art may be used.

The pharmaceutical composition of the present invention can be administered to mammals including humans by any route of administration. It can be administered orally or parenterally. Parenteral administration methods include, for example, but are not limited thereto, intravenous, intramuscular, intraarterial, intramedullary, intrathecal, intracardiac, transdermal, subcutaneous, intraperitoneal, intranasal, intestinal, topical, sublingual or rectal administration. For example, the pharmaceutical composition of the present invention may be prepared in an injectable formulation and administered by a method of lightly pricking the skin with a 30 gauge thin injection needle, or directly applying it to the skin.

The pharmaceutical composition of the present invention may be formulated as a formulation for oral administration or parenteral administration according to the route of administration as described above.

In the case of a formulation for oral administration, the composition of the present invention may be formulated using a method known in the art such as powder, granule, tablet, pill, dragee, capsule, liquid, gel, syrup, slurry, suspension, etc. For example, oral preparations can be obtained as a tablet by blending the active ingredient with a solid excipient, pulverizing it, adding a suitable adjuvant, and processing it into a granule mixture. Examples of suitable excipients include diluents such as sugars including as lactose, dextrose, sucrose, sorbitol, mannitol, xylitol, erythritol and maltitol; starches including corn starch, wheat starch, rice starch and potato starch; celluloses including cellulose, methyl cellulose, sodium carboxymethylcellulose and hydroxypropylmethyl-cellulose; gelatin; polyvinylpyrrolidone; and the like. In addition, in some cases, cross-linked polyvinylpyrrolidone, agar, alginic acid or sodium alginate may be added as a disintegrant. Furthermore, the pharmaceutical composition of the present invention may further comprise an anti-aggregating agent, a lubricant, a wetting agent, a flavoring agent, an emulsifying agent and a preservative.

In the case of a formulation for parenteral administration, it can be formulated in the form of injections, creams, lotions, ointments for external use, oils, moisturizers, gels, aerosols, and nasal inhalants by a method known in the art.

The total dosage of the pharmaceutical composition of the present invention may be administered to a patient as a single dose, and may be administered by a fractionated treatment protocol that is administered for a long time in multiple doses. The pharmaceutical composition of the present invention may vary the content of the active ingredient according to the symptoms of the disease. Preferably, the preferred total dose of the composition of the present invention may be about 0.01 μg to 1,000 mg, most preferably 0.1 μg to 100 mg per 1 kg of the patient's body weight per day. However, the appropriate effective dosage of the pharmaceutical composition of the present invention can be determined by conventional knowledge in the art based on the route of administration and the number of treatments as well as various factors such as the patient's age, weight, health condition, sex, disease severity, diet, and excretion rate. The pharmaceutical composition according to the present invention is not particularly limited to any specific formulation, route of administration, and method of administration as long as it exhibits the effects of the present invention.

In addition, the pharmaceutical composition of the present invention may be administered as an individual therapeutic agent or administered in combination with other therapeutic agents. When administered in combination with other therapeutic agents, the composition of the present invention and the other therapeutic agent(s) may be administered simultaneously, individually or sequentially. At this time, the other therapeutic agent may be a substance already known to have an effect of treating or improving muscular dystrophy. The other therapeutic agent includes all other anti-cancer therapies other than drug therapy, such as radiation therapy.

When the pharmaceutical composition of the present invention is administered in combination with another therapeutic agent, the composition of the present invention and the other therapeutic agent may be separately formulated into separate containers, or may be formulated in combination in the same formulation.

In order to administer the compound presented in the present invention to the human body, a representative pharmaceutical method will be described in detail with tablets as an example. Compounds A and B presented below refer to substances presented as active ingredients for the treatment, improvement or prevention of muscular dystrophy in the present invention.

Composition 1 (unit: mg per tablet)
Compound A: 10
Lactose: 20
Sodium Lauryl Sulfate (SLS): 5
Polyvinyl pyrrolidone (PVP): 2
Sodium Croscarmellose: 5
Magnesium Stearate: 3
Total amount: 45
Composition 2 (unit: mg per tablet)
Compound B: 20
Lactose: 30
Sodium lauryl sulfate (SLS): 10
Polyvinyl pyrrolidone (PVP): 2
Sodium Croscarmellose: 5
Microcrystalline Cellulose: 10
Magnesium Stearate: 3
Total amount: 80

In another aspect of the present invention, there is provided a method for treating or preventing (progressive) muscular dystrophy comprising administering to a subject a compound or composition of the present invention.

In the method for treating or preventing (progressive) muscular dystrophy according to the present invention, each term has the same meaning as above in the pharmaceutical composition for treating or preventing (progressive) muscular dystrophy, unless otherwise specified.

As used herein, the term "subject" includes any human or non-human animal. The term "non-human animal" may be a vertebrate, such as non-human primates, sheep, dogs, and rodents, such as mice, rats, and guinea pigs. The subject may preferably be a human. The term "subject" is used interchangeably herein with "object" and "patient".

In the method for treating or preventing (progressive) muscular dystrophy according to the present invention, the composition of the present invention may be administered to a subject simultaneously, sequentially, or separately with other therapeutic agent(s). The "simultaneous" administration means that the composition of the present invention and another therapeutic agent are administered at the same time through the same administration method. The "sequential" administration means administering the composition of the present invention and another therapeutic agent using separate administration methods, but relatively sequentially, allowing the minimum possible time as the time consumed in the administration interval. The "individual" administration refers to administration of the composition of the present invention and another therapeutic agent at regular time intervals. The administration method of the composition of the present invention and other therapeutic agents may be appropriately selected by a person skilled in the art in consideration of the therapeutic efficacy and side effects of the patient.

Advantageous Effects

The compounds according to the invention provide significant therapeutic, prophylactic and ameliorating effects on (progressive) muscular dystrophy. Accordingly, the composition comprising the compound according to the present invention can be applied as a pharmaceutical composition for preventing or treating (progressive) muscular dystrophy. In particular, the compound according to the present invention has an improved effect compared to the existing ataluren.

BRIEF DESCRIPTION OF THE DRAWINGS

FIG. 1 shows the concentration-time trend of ataluren in the blood after a single oral administration of the compound of Example 3. In FIG. 1, Δ denotes the administration group of Example 3 compound, and ▲ denotes the administration group of ataluren, standard substance.

DETAILED DESCRIPTION

Hereinafter, examples and the like will be described in detail to help the understanding of the present invention. However, the embodiments according to the present invention may be modified in various other forms, and the scope of the present invention should not be construed as being limited to the following examples. The examples of the present invention are provided to more completely explain the present invention to those of ordinary skill in the art to which the present invention pertains.

First, examples of the compound of Chemical Formula 1 according to the present invention are described below. Representative examples along with specific preparation steps are described below, and compounds having different substituents may be prepared through similar steps. Those of ordinary skill in the art will be able to easily prepare compounds of Chemical Formula 1 with different substituents with reference to the following representative examples.

Example 1

1-(3-hydroxy-3-methylbutanoyloxy)ethyl 3-(5-(2-fluorophenyl)-1,2,4-oxadiazol-3-yl)benzoate

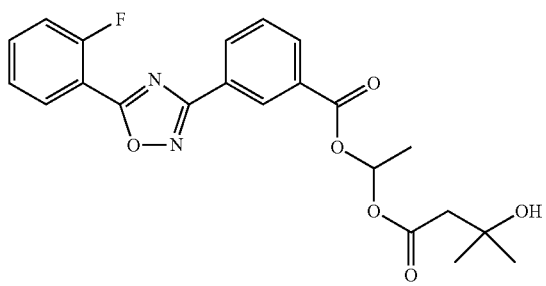 [SMILES: CC(OC(=O)CC(C)(C)O)OC(=O)c1cccc(-c2noc(-c3ccccc3F)n2)c1]

200 mg of ataluren, 127 mg of 1-chloroethyl 3-hydroxy-3-methylbutanoate and 688 mg of cesium carbonate were suspended in 10 ml of acetonitrile. It was stirred under reflux overnight and then concentrated. After dilution with 10 ml of water, the mixture was extracted three times with 10 ml of dichloromethane, dried over anhydrous magnesium sulfate, concentrated again, and purified by silica gel chromatography (5% methanol, dichloromethane) to obtain 210 mg of the compound as a white solid.

$^1$H NMR (400 MHz, CDCl$_3$) 1.25 (6H, s), 1.72 (3H, d), 2.40 (2H, s), 5.55 (1H, q), 7.25-7.32 (2H, m), 7.61-7.65 (2H, m), 8.10-8.25 (2H, m), 8.22 (1H, d), 8.80 (1H, s)

Example 2

(3-hydroxy-3-methylbutanoyloxy)methyl 3-(5-(2-fluorophenyl)-1,2,4-oxadiazol-3-yl)benzoate

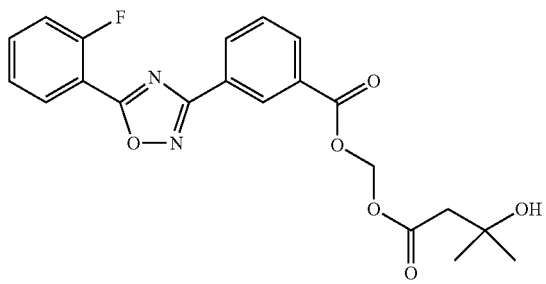

200 mg of ataluren, 117 mg of chloromethyl 3-hydroxy-3-methylbutanoate and 688 mg of cesium carbonate were suspended in 10 ml of acetonitrile. It was stirred under reflux overnight and then concentrated. After dilution with 10 ml of water, the mixture was extracted three times with 10 ml of dichloromethane, dried over anhydrous magnesium sulfate, concentrated again, and purified by silica gel chromatography (5% methanol, dichloromethane) to obtain 190 mg of the compound as a white solid.

$^1$H NMR (400 MHz, CDCl$_3$) 1.23 (6H, s), 2.33 (2H, s), 6.85 (2H, s), 7.15-7.32 (2H, m), 7.50-7.63 (2H, m), 8.06-8.15 (2H, m), 8.18 (1H, d), 8.76 (1H, s)

Example 3

2-(3-hydroxy-3-methylbutanoyloxy)ethyl 3-(5-(2-fluorophenyl)-1,2,4-oxadiazol-3-yl)benzoate

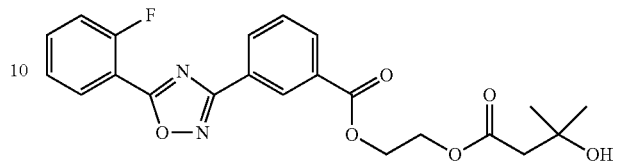

200 mg of ataluren and 227 mg of 2-hydroxyethyl 3-hydroxy-3-methylbutanoate were suspended in 7 ml of tetrahydrofuran. 201 mg of 1-ethyl-3-(3-dimethylaminopropyl)carbodiimide hydrochloride and 86 mg of dimethylaminopyridine were added, stirred overnight, and then concentrated. After dilution with 10 ml of water, the mixture was extracted three times with 10 ml of dichloromethane, dried over anhydrous magnesium sulfate, concentrated again, and purified by silica gel chromatography (3% methanol, dichloromethane) to obtain 314 mg of the compound as an oil. A small amount of normal hexane was added thereto and left for 2 days to obtain 250 mg of the above compound as a white solid.

$^1$H NMR (400 MHz, CDCl$_3$) 1.28 (6H, s), 2.56 (2H, s), 4.50 (2H, t), 4.59 (2H, t), 7.28-7.35 (2H, m), 7.60-7.65 (2H, m), 8.18-8.25 (2H, m), 8.39 (1H, d), 8.83 (1H, s)

Example 4

4-(3-hydroxy-3-methylbutanoyloxy)benzyl 3-(5-(2-fluorophenyl)-1,2,4-oxadiazol-3-yl)benzoate

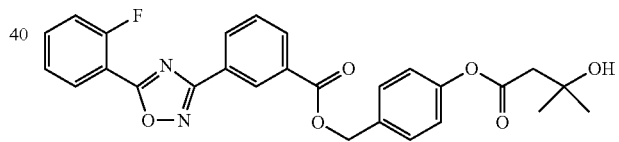

150 mg of ataluren and 178 mg of 4-(hydroxymethyl)phenyl 3-hydroxy-3-methylbutanoate were suspended in 6 ml of tetrahydrofuran. 151 mg of 1-ethyl-3-(3-dimethylaminopropyl)carbodiimide hydrochloride and 65 mg of dimethylaminopyridine were added, stirred overnight, and then concentrated. After dilution with 10 ml of water, the mixture was extracted three times with 10 ml of dichloromethane, dried over anhydrous magnesium sulfate, concentrated again, and purified by silica gel chromatography (3% methanol, dichloromethane) to obtain 242 mg of the compound as a white solid.

$^1$H NMR (400 MHz, CDCl$_3$) 1.38 (6H, s), 2.76 (2H, s), 5.40 (2H, s), 7.11 (2H, d), 7.25-7.35 (2H, m), 7.50 (2H, d), 7.60-7.63 (2H, m), 8.23-8.27 (2H, m), 8.38 (1H, d), 8.85 (1H, s)

Example 5

Pharmacokinetic Evaluation

A pharmacokinetic study of Example 3 compound was performed as follows. That is, after a single oral administration of a test substance to SD (Sprague-Dawley) rats, the efficacy of the compound of the present invention was verified by tracking the kinetics of ataluren released into the blood by metabolic process and comparing it with a standard substance. Specifically, after preparing the test substance (Example 3 compound and ataluren standard, respectively), a single oral administration at a dose of 0.141 mol/kg to rats was performed, and blood was collected at a predetermined time, and then plasma was separated. Analysis of the drug was performed using HPLC (XBridge column $C_{18}$, Waters, Mobile phase 0.1% formic acid:acetonitrile (35:65, %/%)) and MS/MS (ESI positive, MRM). A calibration solution of 5, 50, 100, 500, 1000 and 5000 ng/ml was prepared by mixing the rat blank plasma and each standard solution in a ratio of 9:1, and the calibration was performed therewith. In addition, QC sample was prepared as 100, 750 and 2500 ng/ml concentration by mixing rat blank plasma and standard solution for QC in a ratio of 9:1. As for the pretreatment method, 100 μl of the plasma sample was transferred to a centrifuge tube, 10 μl of the internal standard solution and 300 μl of methanol were added and mixed for about 30 seconds. The tube was centrifuged at 3000×g (4° C.) for about 5 minutes, and the supernatant was transferred to an LC vial and then injected into the instrument. And the concentration of the active ingredient, that is, ataluren in rat plasma was quantified by applying a previously verified assay. For pharmacokinetic parameters, WinNonlin 5.2 (Pharsight, USA) program was used, and $AUC_{0-t}$, $AUC_{0-\infty}$, $C_{max}$, $T_{max}$, and $t_{1/2}$ were calculated by noncompartment modeling (best fit). Pharmacokinetic parameter results were expressed as mean (Mean) and standard deviation (SD), and were statistically processed using the SPSS program (Statistical Package for the Social Sciences, 10.0K, USA).

As a result of the test, after oral administration of Example 3 compound (0.141 mmol/kg, n=3), the mean $AUC_t$ of ataluren in plasma was 327171 hr*ng/ml, the mean $AUC_i$ was 335533 hr*ng/ml, and the mean $C_{max}$ was 26560 ng/ml. The average $T_{max}$ of ataluren was 2.00 hr, and the average $t_{1/2}$ was 3.93 hr, and the bioavailability was 123.1% compared to that of orally administered standard substance. The trend of ataluren blood concentration over time after oral administration of Example 3 compound is shown in FIG. 1.

Assessment of Ataluren Blood Concentration After Administration

TABLE 1

| Compound administered Dose (n = 3) | $AUC_t$ hr * ng/ml | $AUC_i$ hr * ng/ml | Cmax ng/ml | Tmax hr | $t_{1/2}$ hr |
|---|---|---|---|---|---|
| Example 3 0.141 mmol/kg | 327,171 | 335,533 | 26,560 | 2.00 | 3.93 |
| ataluren 0.141 mmol/kg | 265,692 | 266,618 | 28,049 | 8.00 | 2.08 |

As shown in Table 1, not only the bioavailability of the compound according to the present invention was greatly improved compared to ataluren, but also the onset time of the drug was able to be accelerated, and in particular, it was confirmed that the duration of the drug effect could be extended through the increased half-life.

What is claimed is:

1. A compound represented by Chemical formula 1

[Chemical Formula 1]

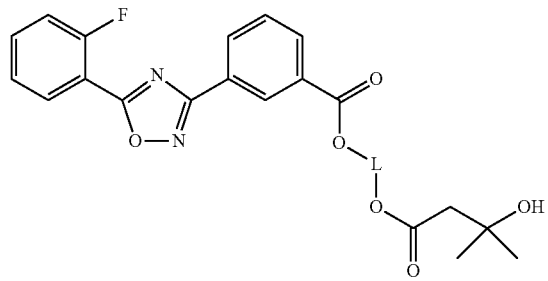

wherein L is selected from the group consisting of straight or branched alkyl having 1 to 3 carbon atoms and benzyl.

2. The compound according to claim 1, wherein the compound is
1-(3-hydroxy-3-methylbutanoyloxy)ethyl 3-(5-(2-fluorophenyl)-1,2,4-oxadiazol-3-yl)benzoate;
(3-hydroxy-3-methylbutanoyloxy)methyl 3-(5-(2-fluorophenyl)-1,2,4-oxadiazol-3-yl)benzoate;
2-(3-hydroxy-3-methylbutanoyloxy)ethyl 3-(5-(2-fluorophenyl)-1,2,4-oxadiazol-3-yl)benzoate; or
4-(3-hydroxy-3-methylbutanoyloxy)benzyl 3-(5-(2-fluorophenyl)-1,2,4-oxadiazol-3-yl)benzoate.

3. A pharmaceutical composition, comprising the compound of claim 1 as an active ingredient.

4. The pharmaceutical composition according to claim 3, wherein the compound is
1-(3-hydroxy-3-methylbutanoyloxy)ethyl 3-(5-(2-fluorophenyl)-1,2,4-oxadiazol-3-yl)benzoate;
(3-hydroxy-3-methylbutanoyloxy)methyl 3-(5-(2-fluorophenyl)-1,2,4-oxadiazol-3-yl)benzoate;
2-(3-hydroxy-3-methylbutanoyloxy)ethyl 3-(5-(2-fluorophenyl)-1,2,4-oxadiazol-3-yl)benzoate; or
4-(3-hydroxy-3-methylbutanoyloxy)benzyl 3-(5-(2-fluorophenyl)-1,2,4-oxadiazol-3-yl)benzoate.

5. A method for treating muscular dystrophy, comprising: administering to a subject in need thereof a therapeutically effective amount of the compound of claim 1.

6. The method according to claim 5, wherein the muscular dystrophy is progressive muscular dystrophy.

7. The method according to claim 5, wherein the muscular dystrophy is Duchenne muscular atrophy.

8. The method according to claim 5, wherein the compound is
1-(3-hydroxy-3-methylbutanoyloxy)ethyl 3-(5-(2-fluorophenyl)-1,2,4-oxadiazol-3-yl)benzoate;
(3-hydroxy-3-methylbutanoyloxy)methyl 3-(5-(2-fluorophenyl)-1,2,4-oxadiazol-3-yl)benzoate;
2-(3-hydroxy-3-methylbutanoyloxy)ethyl 3-(5-(2-fluorophenyl)-1,2,4-oxadiazol-3-yl)benzoate; or
4-(3-hydroxy-3-methylbutanoyloxy)benzyl 3-(5-(2-fluorophenyl)-1,2,4-oxadiazol-3-yl)benzoate.

* * * * *